(12) United States Patent
Loenders et al.

(10) Patent No.: US 7,504,540 B2
(45) Date of Patent: Mar. 17, 2009

(54) PROCESS FOR OBTAINING AMINES BY REDUCTION OF AMIDES

(75) Inventors: Raf Loenders, Bierbeck (BE); Ivan Vanden Eynde, Keerbergen (BE); Piet Vanneste, Denderwindeke (BE)

(73) Assignee: Taminco N.V., Gent (BE)

( * ) Notice: Subject to any disclaimer, the term of this patent is extended or adjusted under 35 U.S.C. 154(b) by 81 days.

(21) Appl. No.: 11/621,222

(22) Filed: Jan. 9, 2007

(65) Prior Publication Data

US 2007/0191642 A1 Aug. 16, 2007

Related U.S. Application Data

(63) Continuation-in-part of application No. 11/157,141, filed on Jun. 21, 2005, now abandoned.

(51) Int. Cl.
*C07C 209/50* (2006.01)
(52) U.S. Cl. ...................................... 564/488
(58) Field of Classification Search ...................... None
See application file for complete search history.

(56) References Cited

U.S. PATENT DOCUMENTS

| 2,166,971 A | 7/1939 | Schmidt et al. |
| 2,187,745 A | 1/1940 | Lazier |
| 3,190,922 A | 6/1965 | Bard et al. |
| 3,444,204 A * | 5/1969 | Hartwig ...................... 564/480 |
| 5,075,505 A | 12/1991 | Forquy et al. |
| 5,840,985 A | 11/1998 | Nepras et al. |

OTHER PUBLICATIONS

Pashkova L. P. et al: "Hydrogenation of N,N-Dimethylamides of Fatty Acids to the Corresponding Dimethylalkylamines", Journal of Applied Chemistry of USSR, Consultants Bureau, New York, NY, US, vol. 53, No. 8, Aug. 1981, pp. 1398-1401, XP009042781 ISSN: 0021-888X.

* cited by examiner

*Primary Examiner*—Brian J Davis
(74) *Attorney, Agent, or Firm*—Sughrue Mion, PLLC

(57) ABSTRACT

Disclosed is a process for the preparation of primary, secondary and tertiary amines via a catalytic hydrogenation of unsubstituted, N-substituted, and N,N-disubstituted amides. The amide is led, together with an auxiliary amine, in vaporised form in a hydrogen containing gas flow over the catalyst. The process can be carried out at relatively low pressures, between 2 and 50 bars, using typical hydrogenation catalysts like CuCr-type catalysts. The amine is obtained with high yield and high selectivity. The process can be carried out in a continuous fixed bed reactor.

23 Claims, No Drawings

PROCESS FOR OBTAINING AMINES BY REDUCTION OF AMIDES

This is a Continuation-in-Part of application Ser. No. 11/157,141 filed Jun. 21, 2005 now abandoned. The entire disclosure of the prior application, application Ser. No. 11/157,141, is hereby incorporated by reference.

BACKGROUND OF THE INVENTION

The present invention relates to an improved process for obtaining amines with the following formula

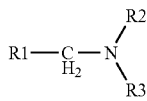

by catalytic reduction of the corresponding amide. The amines should be obtained with high yield and purity. They can be used in a broad range of applications including agrochemicals, pharmaceuticals, detergents, personal care . . .

PRIOR ART

There are several well described processes for obtaining such amines. Aldehydes, ketons or alcohols react with ammonia or amines under reductive conditions to form primary, secondary or tertiary amines. Another route starts from nitrites, which are reduced to primary amines and if necessary transformed to tertiary amines by reaction with formaldehyde. For speciality products, like pharmaceutical intermediates, the starting material is often an organic halogenide, which reacts readily with ammonia or an amine to form an organic amine salt. High value amine products can also be obtained by reducing amides with powerful reducing agents like $LiBH_4$ or $AlH_3$.

However, when using catalytic hydrogenation the amide reduction route becomes attractive for producing a broad range of amines, especially for bulk processes. For the production of fatty dimethylamines for instance, the fatty amide can be easily obtained by reacting the fatty acid with dimethylamine. By reducing this amide the desired amine is obtained. This route offers an economically interesting alternative for the fatty alcohol or fatty nitrile route (currently used to produce fatty amines). Patents describing the catalytic hydrogenation of fatty amides have been published since the early 60s (see for example U.S. Pat. No. 3,190,922, U.S. Pat. No. 3,444,204). Until now, however, processes describing the reduction of amides are not very appealing due to low activity and/or side product formation; especially fatty alcohol and dialkylamines (containing a further R1-CH2 group instead of an R2 or an R3 group).

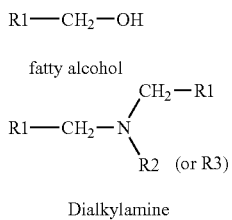

Dialkylamine

The dialkylamine side products will increase the distillation residue while fatty alcohols, due to little difference in boiling temperature, cannot be separated from the fatty amine and thus reduce the product quality.

In the prior art the catalytic hydrogenation of fatty amides has been performed either in a liquid or in a gaseous phase.

When working in slurry, with recycle of hydrogen, the reaction is usually carried out under a relatively low reaction pressure, i.e. under reaction pressures lower than 55 bars. A number of patent publications which describe a liquid phase slurry process to produce an alkyldimethyl amine, namely U.S. Pat. No. 3,190,922, U.S. Pat. No. 5,840,985 and U.S. Pat No. 5,075,505, teach to add DMA (dimethylamine) in order to reduce the formation of fatty alcohol. However, it appears for example from comparative example 1 of U.S. Pat. No. 5,840,985, from example 2 of U.S. Pat. No. 5,075,505 and from example 5 of U.S. Pat. No. 3,190,922 that although the addition of DMA contributes to solving the problem of the alcohol formation it does not help to solve the problem of the dialkylamine side products which are formed. On the contrary, when comparing example 5 of U.S. Pat. No. 3,190,922 with example 1 thereof, it even appears that the addition of DMA increases the formation of these dialkylamine side products.

U.S. Pat. No. 5,840,985 discloses to solve the problem of the dialkylamine side product formation by addition of sodiummethoxide to the solution. The addition and removal of this salt is of course reflected in the overall economics of the process. Moreover, the scale up of these slurry processes is not straightforward among others due to the difficult catalyst recycle. Especially continuous operation becomes a difficult issue. Moreover, there is a real risk of catalyst (like CuCr, Ni, . . . ) ending up in the product.

The known fixed bed processes wherein the amide is at least partially led in the gaseous phase over the catalyst can also not compete with the fatty alcohol or nitrile processes. Pashkova, L. P.; Yakashkin, M. I. Zhurnal Prikladnoi Khimii, Vol. 53, No. 8, pp 1834-1837 disclose a process wherein the hydrogenation reaction is carried out at atmospheric pressure. Hydrogen is supplied to the reactor at a molar hydrogen/amide ratio of 10/1. Notwithstanding the use of such a relatively high amount of hydrogen and notwithstanding the fact that in the examples the amide was only led over the catalyst at a flow rate of 0.16 g/g catalyst/hour, not only selectivity but also conversion is low. The reaction product contained, apart from a small amount of alcohol, a large amount of other side products.

In order to increase the conversion, the hydrogenation reaction can be performed under higher reaction pressures as disclosed for example in U.S. Pat. No. 3,444,204. This US patent discloses a pressure range of between 50 and 300 atmospheres but all of the examples are performed at a pressure of 250 or 260 atmospheres At such high pressures activity is reasonably good, but from the examples of U.S. Pat. No. 3,444,204 it appears that the selectivity or yield is still low due to the formation of the undesired dialkylamines (see for example Example 1 of U.S. Pat. No. 3,444,204; ca. 4.5% of dialkylmethylamine is formed) and, in case of more realistic catalyst contact times, also due to the formation of alcohols (see for example Example 2 of U.S. Pat. No. 3,444,204). A further important drawback of the hydrogenation process disclosed in U.S. Pat. No. 3,444,204 is that the use of the high reaction pressures implicate high construction and operation costs. In the process disclosed in U.S. Pat. No. 3,444,204 the high reaction pressure appears however to be essential to achieve the best possible yield, although this yield is still too low.

According to the present inventors the fact that the process disclosed in U.S. Pat. No. 3,444,204 requires high reaction pressures to optimise the yield can be explained as follows. When a film of liquid is formed onto the surface of the catalyst a high pressure is required to achieve a sufficient hydrogen concentration on the surface of the catalyst. As appears for example from c. 4, l. 16-20 of U.S. Pat. No. 5,075,505 hydrogen diffuses indeed badly into the amide. Such a diffusion is however required in the process disclosed in U.S. Pat. No. 3,444,204 since, under the high pressures used in that process, a large portion of the amide will still be in liquid form notwithstanding the fact that a lot of hydrogen is used. In fact in examples 1 and 2 only about 20 wt % of the amide will be in the vapour form due to the low vapour pressure of the amide combined with the high pressure in the reactor. Consequently, a film of liquid amide and reaction products will be present on the surface of the catalyst wherein the hydrogen has to diffuse to be able to react. This diffusion is enhanced by the use of higher hydrogen pressures so that, in the process described in U.S. Pat. No. 3,444,204, the use of pressures higher than 50 atmospheres is essential to achieve a good conversion.

An object of the present invention is to provide a process for preparing amines in the gaseous phase by catalytic reduction of an amide which enables to achieve the amines with higher yield and purity. The amine corresponds to the following formula:

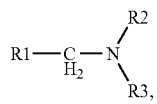

wherein R1 is H or a saturated or unsaturated hydrocarbon group containing from 1 to 23 carbon atoms and wherein R2 and R3 are independently H or a hydrocarbon group containing from 1 to 8 carbon atoms, and preferably 1 to 4 carbon atoms, and the amine is obtained by reducing an amide of the following formula:

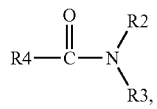

wherein R4 is equal to R1 but may show a different degree of unsaturation, with hydrogen by means of a hydrogenation catalyst. Usually, R1 is a saturated or unsaturated hydrocarbon group containing at least 1 carbon atoms, in particular at least 3 carbon atoms, more particularly at least 5 carbon atoms and especially at least 7 carbon atoms. R1 preferably contains at the most 20 carbon atoms, more preferably at the most 18 carbon atoms. R2 and R3, on the other hand, are usually a hydrocarbon group containing from 1 to 8 carbon atoms, and in particular 1 to 4 carbon atoms.

SUMMARY OF THE INVENTION

To achieve the object of the invention, the process is characterised in that the amide is reduced by means of hydrogen in the presence of an auxiliary amine of the following formula:

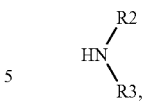

and in that the hydrogen, the auxiliary amine and the amide are all led at least substantially completely in a gaseous form, in a gaseous stream, over the hydrogenation catalyst at a reaction pressure higher than 2 but lower than 50 bars.

It was found that when working entirely or at least substantially entirely in the gaseous phase at reasonable low pressures (2-50 bars) and adding an auxiliary amine, high activity and very high selectivity towards the desired amine can be obtained using typical hydrogenation catalysts. At pressures of between 2 and 50 bars, it is economically feasible to use the amount of hydrogen (optionally in combination with an additional carrier gas) which is required to vaporise all of the amide in the feedstream. At the pressures used in the examples of U.S. Pat. No. 3,444,204 it is on the contrary almost not feasible to use an amount of hydrogen which would vaporise all of the amide. The present inventors have done tests showing indeed that the saturated vapour pressure of dimethyllaurylamide at 250° C. comprises about 220 mbar. At 250 bar, more than 1000 mol $H_2$/mol dimethyllaurylamide would thus be required for complete amide vaporisation. In the examples given in U.S. Pat. No. 3,444,204 much less hydrogen is however used, more particularly such an amount that only a minor part of the amide is actually in the vapour form.

Surprisingly, in the process according to the invention the lower reaction pressure does not result in lower activity. On the contrary, even higher activity was obtained. An important advantage of the relatively low pressures applied in the process according to the invention, is indeed that they enable to use the amount of hydrogen (optionally in combination with other carrier gasses) required to vaporise all of the amide. In this way no liquid film is formed on the catalyst so that no high reaction pressure is required to allow the hydrogen to reach the catalyst surface. The combination of a relatively low pressure, a sufficiently high amount of hydrogen and optionally other gasses to vaporise all of the reactants and the use of an auxiliary amine was thus found quite surprisingly to enable to obtain a high activity and a very high selectivity towards the desired amine using typical hydrogenation catalysts. The addition of the auxiliary amine did not only reduce the alcohol content in the product, but surprisingly also the formation of the undesired dialkylamines. The low dialkylamine formation is not only important to obtain high yields of the desired amine product, but in case of gasphase operation the high boiling dialkylamines could form a liquid film around the catalyst, blocking the active sites and reducing its activity and life time. This is thus prevented in the process according to the invention by the addition of the auxiliary amine.

In a preferred embodiment of the process according to the invention, the hydrogen and the auxiliary amine are led together with said amide in such an amount over the hydrogenation catalyst that the obtained reaction product contains less than 2 parts by weight, preferably less than 1 part by weight and more preferably less than 0.5 parts by weight of the alcohol $R1CH_2OH$ per 100 parts by weight of the sum of said amine, said amide, the alcohol $R1CH_2OH$ and of the undesired dialkylamines $(R1CH_2)_2NR2$ and $(R1CH_2)_2NR3$. In a further preferred embodiment of the process according to the invention, the hydrogen and the auxiliary amine are led together with said amide in such an amount over the hydrogenation catalyst that the obtained reaction product contains less than 5 parts by weight, preferably less than 3 parts by weight and more preferably less than 2 parts by weight of the sum of the undesired dialkylamines (R1CH$_2$)$_2$NR2 and (R1CH$_2$)$_2$NR3 per 100 parts by weight of the sum of said amine, said amide, the alcohol R1CH$_2$OH and the undesired dialkylamines (R1CH$_2$)$_2$NR2 and (R1CH$_2$)$_2$NR3.

By using a sufficient amount of hydrogen and of auxiliary amine in the gaseous feed stream, a high selectivity can thus be obtained. The % selectivity is usually given by the following equation:

% selectivity=(number of moles of the desired amine obtained/number of moles of the desired amine theoretical)*100.

In the present specification, the number of moles of the desired amine obtained includes the number of moles of any secondary amine when the amine to be obtained is a tertiary amine wherein R2 and R3 are the same. By a simple additional alkylation step, the secondary amine can indeed be easily converted into the desired tertiary amine. In the process according to the invention, the desired amine, including any secondary amine when said amine is a tertiary amine wherein R2 and R3 are the same, is preferably produced in greater than 90% selectivity, more preferably in greater than 95% selectivity by leading said amide over the catalyst with a sufficient contact time and by providing said hydrogen and said auxiliary amine in a sufficient amount in the gaseous stream.

In a particular embodiment of the process according to the invention, the gaseous stream which is led over the catalyst is composed to contain, per mole of said amide, in total at least $N_c$ moles of carrier gasses which comprise at least said auxiliary amine and said H$_2$; with $$N_c = \frac{P_{tot} - VP_a}{VP_a}$$

wherein: $P_{tot}$=the reaction pressure; and
$VP_a$=the saturated vapour pressure of the amide at the reaction temperature.

When using such an amount of carrier gasses, the amide is led entirely in vapour form over the catalyst. Indeed, with such an amount of carrier gasses, the amide is completely vaporised since the partial pressure of the amide is lower than the saturated vapour pressure of the amide at the reaction temperature.

Depending on the starting amide and auxiliary amine, the reaction conditions may differ in temperature, pressure, H$_2$ flow and catalyst.

In practice the carrier gas consists predominantly out of H$_2$ with small quantities of auxiliary amine. Mixtures of H$_2$ and inert gasses like N$_2$ or He are also possible.

By operating like this, a very pure amine product can be obtained, containing no or low unreacted amide and alcohol and only minor amounts of mixed amines by-products. Depending on the application, the obtained product can be used as such or requires a simple purification.

On top of that, the catalyst does not suffer from rapid deactivation. The free access of H$_2$ on the catalysts, protecting it from poisons in the feed or poisonous reaction intermediates, may explain this prolonged life compared to liquid and trickling phase reactions.

The process can be easily operated as a fixed bed process. This offers important advantages over slurry processes, such as a straightforward continuous operation, simple process follow up and no catalyst ending up in the product. The unreacted H$_2$ and auxiliary amines can be easily separated from the product and recycled The low operation pressure of this invention, compared to the known fixed bed processes, reduces significantly the construction costs and moreover lowers drastically the extremely high H$_2$ excess or additional inert carrier gas (and thus recycle stream) necessary to vaporise the high boiling amides.

DETAILED DESCRIPTION OF THE INVENTION

The present invention relates to a process for the production of primary, secondary or tertiary amines of following formula:

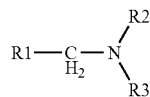

wherein R1 is H or a saturated or unsaturated hydrocarbon group containing from 1 to 23 carbon atoms and wherein R2 and R3 are independently H or a hydrocarbon group containing from 1 to 8 carbon atoms.

The process comprises the reduction with H$_2$ of an amide of following formula:

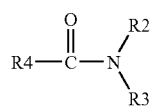

wherein this amide is led together with an auxiliary amine of following formula:

in a gaseous stream which contains the H$_2$, over a hydrogenation catalyst. In the formula of said amide, R4 is equal to R1 but may show a different degree of saturation. Notice that, in case R2 and R3 are both H, the auxiliary amine is in fact ammonia which has in the present specification also to be understood as being an amine. An essential feature of the process according to the invention is that the entire amount of the amide which is led over the catalyst is led in gaseous form over the catalyst. This is achieved by using a sufficient amount of hydrogen, optionally in combination with one or more additional carrier gasses.

The reaction is carried out at a relatively low pressures in the range of between 2 and 50 bars. In view of obtaining a still higher activity, the reaction pressure is preferably higher or equal to 3 bars, more preferably higher or equal to 4 bars and most preferably higher or equal to 5 bars. Since the required amount of carrier gas increases considerably with higher pressures, the reaction pressure is preferably lower than 45 bars, more preferably lower than 30 bars and most preferably lower than 20 bars.

The amount of carrier gasses is selected in such a manner that all of the reactants are at least substantially entirely vaporised. This is achieved when use is made, per mole of amide, of a total at least $N_c$ moles of carrier gasses which comprises the hydrogen, the less important amount of auxiliary amine and any further substances (carrier gasses) which are gaseous under the reaction conditions, with $$N_c = \frac{P_{tot} - VP_a}{VP_a}$$

wherein: $P_{tot}$=the total reaction pressure; and
$VP_a$=the saturated vapour pressure of the amide at the reaction temperature.

For an amide having a saturated vapour pressure of about 220 mbar at the reaction temperature, $N_c$ is for example equal to:
- 22 for a reaction pressure of 5 bars;
- 44 for a reaction pressure of 10 bars;
- 90 for a reaction pressure of 20 bars;
- 226 for a reaction pressure of 50 bars; and
- 1135 for a reaction pressure of 250 bars.

Typical reaction temperatures range from 100 to 350° C. and $H_2$ dilution varies from 5 to 500 mole/mole amide, all depending on the volatility of the reagents and products as well as on the working pressure and catalyst type. Usually, the reaction temperature will be comprised between 100 and 310° C., more particularly between 100 and 290° C., to prevent any undesired thermal decomposition reactions.

The reaction is catalysed by typical hydrogenation catalysts. These are usually metal based like Cu, Cr, Ni, Co, Pd, Pt, Ru or mixtures thereof, optionally on support and in the presence of modifiers like Li, Na, K, Ba, Mg, Ca, Mn, Zr. The most preferred catalyst is a CuCr-type of catalyst.

The addition of the auxiliary amine strongly reduces the side product formation, in particular alcohol but surprisingly also dialkylamine, when the reaction is performed at least substantially entirely in the gaseous phase as in the process according to the present invention. In a preferred embodiment of the present invention the auxiliary amine/amide mole ratio varies from 0.05 to 40, and is preferably higher than 0.4, more preferably higher than 0.6. In a preferred embodiment, the auxiliary amine/amide mole ratio is lower than 30, preferably lower than 15, and most preferably lower than 5. The lower the auxiliary amine/amide ratio, the higher the side product formation while higher ratios are not desired for reasons of capacity loss and large amine recycle streams. Due to absence of consumption, the auxiliary amine can be recycled. Also addition of large quantities of tertiary auxiliary amines $((R2)_3N)$ do not effect the selectivity, on the contrary and surprisingly, an improvement of the selectivity could be observed in cases where R2 and R3 are the same and consist of a hydrocarbon group with 1 to 4 carbon atoms.

In view of the high selectivity and activity of the process according to the invention, the amide and other reactants can be led at a relatively high flow rate over the catalyst, notwithstanding the fact that the amide is quite diluted in the carrier gas. In view of obtaining a high selectivity, especially to avoid alcohol and undesired dialkylamines in the product stream, the amount of catalyst, or in other words the contact time with the catalyst, is preferably sufficient to convert more than 95 wt %, preferably more than 98 wt %, and more preferably more than 99 wt % of the amide. The catalyst is preferably a fixed bed catalyst.

If the desired amine is a tertiary amine with R2 and R3 being the same, any secondary amine present in the product which is separated off from the gaseous stream which has passed over the catalyst can be converted quite easily to the desired tertiary amine by an additional alkylation step.

EXAMPLE 1

In a fixed bed reactor containing 15 g of CuCr catalyst (Leuna 1970T) a mixture of N,N-dimethyldecylamide, DMA and $H_2$ is introduced. The mixture with a molar composition of amide/auxiliary amine/$H_2$ of 1/3/120 is preheated and introduced continuously at the catalyst bed at a rate of 15 g amide/h. The reactor is heated at 250° C. and operated at 10 bars. At the outlet, the product containing the amine is separated from the gas by condensation. The liquid outlet is analysed using gaschromatography, the composition (area %) is displayed in table 1. By a simple methylation reaction, N-methyldecylamine can be converted to N,N-dimethyldecylamine reducing the side products to less than 1%.

TABLE 1

| product distribution (GC analysis, area %) | | | | |
|---|---|---|---|---|
| N,N-dimethyl decylamine | N-methyl decylamine | N-methyl didecylamine | N,N-dimethyl decylamide | Decanol |
| 96.3 | 2.7 | 0.7 | Nd | 0.1 |

Nd: not detected

EXAMPLE 2

In a fixed bed reactor containing 50 g of CuCr catalyst (Cu0203 Engelhard) a mixture of N,N-dimethyldodecyl amide, DMA and $H_2$ with following molar ratio 1/3/76 is fed continuously at an amide rate of 20 g/h. Prior to the catalyst bed, the mixture passes a pre-heater at 250° C. The catalyst bed is also heated at 250° C. and the reactor is operated at 5 bars. At the outlet, the product containing the amine is separated from the gas flow (containing the $H_2$ and the auxiliary amine) by condensation. The liquid outlet is analysed daily using gaschromatography, the composition (area %) is displayed in table 2. No deactivation is observed after 1 month of testing.

TABLE 2

| Day | N,N-dimethyl dodecylamine | N-methyl dodecylamine | N-methyl didodecylamine | N,N-dimethyl dodecylamide | dodecanol |
|---|---|---|---|---|---|
| 1 | 97.6 | 1.8 | 0.6 | Nd | Nd |
| 10 | 97.6 | 1.8 | 0.5 | Nd | Nd |
| 30 | 97.5 | 1.8 | 0.6 | Nd | Nd |

Nd: not detected

EXAMPLE 3

In a fixed bed reactor containing 5 g of catalyst (Cu0203 Engelhard) a mixture of N,N-dimethylacetamide, DMA and $H_2$ is introduced. The mixture with a molar composition of amide/auxiliary amine/$H_2$ of 1/3/30 is preheated and introduced continuously at the catalyst bed at a rate of 2 g amide/h. The reactor is heated at 250° C. and operated at 10 bars. At the outlet, the product containing the desired amine is analysed with GC on-line. The product composition (area %) is displayed in table 3

TABLE 3

| N,N-dimethyl ethylamine | N-methyl ethylamine | N-methyl diethylamine | N,N-dimethyl acetamide | ethanol |
|---|---|---|---|---|
| 96.1 | 2.8 | 0.8 | Nd | Nd |

Nd: not detected

EXAMPLE 4

In a fixed bed reactor containing 5 g of catalyst (Leuna 1970T) a mixture of acetamide, $NH_3$ (as auxiliary amine) and $H_2$ is introduced. The mixture with a molar composition of amide/ammonia/$H_2$ of 1/10/30 is preheated and introduced continuously at the catalyst bed at a rate of 2 g amide/h. The reactor is heated at 250° C. and operated at 10 bars. At the outlet, the product containing ethylamine is analysed with on-line GC. The product composition (area %) is displayed in table 4

TABLE 4

| ethylamine | diethylamine | triethylamine | acetamide | ethanol |
|---|---|---|---|---|
| 95.5 | 3.5 | 0.5 | Nd | Nd |

Nd: not detected

COMPARATIVE EXAMPLE A

In the same reactor set up, example 1 is repeated except for the DMA addition. The selectivity towards N,N-dimethyldecylamine is reduced to 92.5%, mainly at expense of N-methyldidecylamine and decanol.

TABLE 5

| N,N-dimethyl decylamine | N-methyl decylamine | N-methyl didecylamine | N,N-dimethyl decylamide | decanol |
|---|---|---|---|---|
| 92.5 | 0.4 | 4.7 | Nd | 2.0 |

Nd: not detected

COMPARATIVE EXAMPLE B

In the same reactor set-up as example 2, containing 50 g of CuCr catalyst (Cu0203 of Engelhard) a N,N-dimethyldodecylamide/DMA/$H_2$ mixture with following composition 1/3/8 (molar) was fed continuously at a rate of 5 g amide/h. The reaction was carried out at 10 bars and 250° C. and the product outlet was analysed daily.

In this experiment the $H_2$ dilution is far too little to vaporise 95% of the reagents, resulting in very poor activity and selectivity. After one week already a catalyst decay is observed.

TABLE 6

| Day | N,N-dimethyl dodecylamine | N-methyl dodecylamine | N-methyl didodecylamine | N,N-dimethyl dodecylamide | dodecanol |
|---|---|---|---|---|---|
| 1 | 30.2 | 5.5 | 22.1 | 41.8 | 0.4 |
| 7 | 24.1 | 4.7 | 26.4 | 44.4 | 0.4 |

The invention claimed is:

1. A process for preparing an amine with following formula:

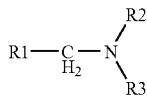

comprising the reduction of an amide of following formula:

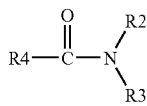

with H$_2$ in the presence of an auxiliary amine of the following formula:

wherein said H$_2$, said auxiliary amine and said amide are all led completely in a gaseous form, in a gaseous stream, over a hydrogenation catalyst, at a reaction pressure higher than 2 but lower than 50 bars, and wherein:

R1 is H or a saturated or unsaturated hydrocarbon group containing from 1 to 23 carbon atoms;

R2 and R3 are independently H or a hydrocarbon group containing from 1 to 8 carbon atoms, and R4 is equal to R1 but may show a different degree of unsaturation.

2. A process according to claim 1, wherein said reduction reaction is performed under a reaction pressure higher than or equal to 3 bars.

3. A process according to claim 1, characterised in that said reduction reaction is performed under a reaction pressure lower than 45 bars.

4. A process according to claim 1, characterised in that said gaseous stream is composed to contain, per mole of said amide, at least N$_c$ moles of carrier gasses which comprise at least said auxiliary amine and said H$_2$; with $$N_c = \frac{P_{tot} - VP_a}{VP_a}$$

wherein: P$_{tot}$=the reaction pressure; and
VP$_a$=the saturated vapour pressure of the amide at the reaction temperature.

5. A process according to claim 1, wherein the auxiliary amine is added in an amount of 0.05 to 40 moles per mole of said amide.

6. A process according to claim 1, wherein R2 and R3 are the same and consist of a hydrocarbon group with 1 to 4 carbon atoms and wherein said reduction is carried out in the presence of said auxiliary amine and in the presence of a further auxiliary amine with following formula:

(R2)$_3$N.

7. A process according to claim 1, wherein after having led the amide and the auxiliary amine in said gaseous stream over the catalyst, a product containing the amine which is to be prepared is separated off from the gaseous stream.

8. A process according to claim 7, wherein the hydrogen and the auxiliary amine are led together with said amide in such an amount over the hydrogenation catalyst that said product contains less than 2 parts by weight of R1CH$_2$OH per 100 parts by weight of the sum of said amine, said amide, R1CH$_2$OH, (R1CH$_2$)$_2$NR2 and (R1CH$_2$)$_2$NR3.

9. A process according to claim 7, wherein the hydrogen and the auxiliary amine are led together with said amide in such an amount over the hydrogenation catalyst that said product contains less than 5 parts by weight of the sum of (R1CH$_2$)$_2$NR2 and (R1CH$_2$)$_2$NR3 per 100 parts by weight of the sum of said amine, said amide, R1CH$_2$OH, (R1CH$_2$)$_2$NR2 and (R1CH$_2$)$_2$NR3.

10. A process according to claim 7, wherein after having separated the amine which is to be prepared off from the gaseous stream, at least a portion of the hydrogen and of the auxiliary amine which are still present is the gaseous stream are recycled to the catalyst.

11. A process according to claim 7, wherein the amine which is to be prepared is a tertiary amine with R2 and R3 being the same and wherein said product is subjected to an alkylation reaction to convert any secondary amine present therein into said tertiary amine.

12. A process according to claim 1, wherein said amide is led over the catalyst with a sufficient contact time to convert more than 95wt % of the said amide.

13. A process according to claim 1, wherein said catalyst is a fixed bed catalyst.

14. A process according to claim 1, wherein R2 and R3 are a hydrocarbon group containing from 1 to 8 carbon atoms.

15. A process according to claim 14, wherein R2 and R3 are a hydrocarbon group containing from 1 to 4 carbon atoms.

16. A process according to claim 1, wherein R1 is a saturated or unsaturated hydrocarbon group containing at least 1 carbon atom.

17. A process according to claim 1, wherein R 1 is a saturated or unsaturated hydrocarbon group containing at the most 20 carbon atoms.

18. A process according to claim 1, wherein said amine, including any secondary amine when said amine is a tertiary amine wherein R2 and R3 are the same, is produced in greater than 90% selectivity.

19. A process according to claim 1, wherein said H$_2$, said auxiliary amine and said amide are led at a temperature of between 100 and 310° C. over the hydrogenation catalyst.

20. A process according to claim 19, wherein said temperature is comprised between 100 and 290° C.

21. A process according to claim 16, wherein R1 is a saturated or unsaturated hydrocarbon group containing at least 3 carbon atoms.

22. A process according to claim 21, wherein R1 is a saturated or unsaturated hydrocarbon group containing at least 5 carbon atoms.

23. A process according to claim 22, wherein R1 is a saturated or unsaturated hydrocarbon group containing at least 7 carbon atoms.

* * * * *